(12) United States Patent
Morrison

(10) Patent No.: US 7,295,309 B1
(45) Date of Patent: Nov. 13, 2007

(54) MICROPARTICLE ANALYSIS SYSTEM AND METHOD

(75) Inventor: Dennis R. Morrison, Kemah, TX (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 339 days.

(21) Appl. No.: 10/734,753

(22) Filed: Dec. 9, 2003

(51) Int. Cl.
*G01N 15/02* (2006.01)

(52) U.S. Cl. ..................................... 356/335
(58) Field of Classification Search ............ None
See application file for complete search history.

(56) References Cited

U.S. PATENT DOCUMENTS

| | | | | |
|---|---|---|---|---|
| 4,075,462 A | * | 2/1978 | Rowe | 377/10 |
| 5,162,863 A | * | 11/1992 | Ito | 356/73 |
| 6,532,061 B2 | * | 3/2003 | Ortyn et al. | 356/28 |
| 6,610,256 B2 | * | 8/2003 | Schwartz | 422/186 |
| 2004/0080747 A1 | * | 4/2004 | Cerni et al. | 356/338 |
| 2004/0260157 A1 | * | 12/2004 | Montes | 600/301 |

* cited by examiner

*Primary Examiner*—Tu T Nguyen
(74) *Attorney, Agent, or Firm*—Kurt G. Hammerle

(57) ABSTRACT

A device for analyzing microparticles is provided which includes a chamber with an inlet and an outlet for respectively introducing and dispensing a flowing fluid comprising microparticles, a light source for providing light through the chamber and a photometer for measuring the intensity of light transmitted through individual microparticles. The device further includes an imaging system for acquiring images of the fluid. In some cases, the device may be configured to identify and determine a quantity of the microparticles within the fluid. Consequently, a method for identifying and tracking microparticles in motion is contemplated herein. The method involves flowing a fluid comprising microparticles in laminar motion through a chamber, transmitting light through the fluid, measuring the intensities of the light transmitted through the microparticles, imaging the fluid a plurality of times and comparing at least some of the intensities of light between different images of the fluid.

26 Claims, 4 Drawing Sheets

Wavelength Specific Light Absorption (per pixel)

Time/Distance in Chamber

MICROPARTICLE ANALYSIS SYSTEM AND METHOD

ORIGIN OF THE INVENTION

The invention described herein was made by an employee of the United States Government and may be manufactured and used by or for the Government of the United States of America for governmental purposes without the payment of any royalties thereon or therefor.

BACKGROUND OF THE INVENTION

1. Field of the Invention

This invention generally relates to the analysis of microparticles or, more specifically, to methods and systems for identifying and counting microparticles.

2. Description of the Related Art

The use and/or detection of particles having diameters ranging from submicrons to a few hundred microns can be useful in a variety of industries. For example, the chemical manufacturing industry may utilize microparticles to distinguish different process liquids and/or identify ownership of liquid products. On the other hand, the pharmaceutical industry sometimes encapsulates drugs or biological therapeutics to form liquid microcapsules. Such microcapsules are used to deliver bioactive components to target organs before the drug or enzyme is released. In this manner, the drug or enzyme may be directed primarily into the target tissue. A "microcapsule", as used herein, may generally refer to a droplet of material synthetically encased with an outer protective shell having a diameter ranging from sub-micron dimensions to a few hundred microns. In contrast, a "microparticle", as used herein, may generally refer to a liquid or solid particle having a diameter ranging from sub-micron dimensions to a few hundred microns. Such a definition of a microparticle may include intentionally and unintentionally formed synthetic and naturally occurring particles. Consequently, a microcapsule is a microparticle, however, a microparticle is not necessarily a microcapsule.

In some cases, it may be beneficial to detect, identify, and count microparticles. For example, in cases in which microparticles are synthetically fabricated, it may be advantageous to identify and count the microparticles during their production for quality assurance purposes. In other applications, such as wastewater processing and/or bulk pumping of industrial chemicals, microparticles may be indicative of contamination. As such, in some embodiments, it may be advantageous to detect and count microparticles to determine the concentration of contaminants within the systems. In some cases, dilution of dyes or taggants may be alternatively used to measure contamination volumes, however, such techniques typically involve taking a sample to a central laboratory for detailed analyses. In addition, some dyes have adverse environmental problems and/or may be very difficult to assay once spilled or evaporated into the air.

Consequently, systems have been developed which are configured to identify and count microparticles. As noted above, microparticles may be used in a variety of applications which have microparticles suspended in fluids such as, waste water processing, bulk pumping of industrial chemicals, and ownership identification of liquid products. Conventional analysis systems, however, often have difficulty in accurately identifying and counting microcapsules which are suspended within fluids. In particular, conventional measurement systems tend to miss microparticles that are moving behind or in the shadow of other microparticles that are in the foreground. As such, quite often, microcapsules have to be removed and collected from the fluid for analysis. As explained in more detail below, however, such a batch-style production process tends to be time-consuming. Conventional systems also have difficulty in distinguishing between known target microparticles, such as microcapsules, and non-target microparticles, such as debris particles and bubbles. As such, obtaining accurate information from conventional systems is sometimes difficult.

Therefore, it would be beneficial to develop a system and method with which to detect, identify and count microparticles accurately and in an efficient manner.

SUMMARY OF THE INVENTION

The problems outlined above may be in large part addressed by systems and methods for analyzing microparticles within flowing fluids. In particular, a device for analyzing microparticles is provided which includes a chamber comprising an inlet and an outlet for respectively introducing and dispensing a flowing fluid comprising microparticles. Such a chamber may be adapted to induce a laminar flow of the fluid such that the microparticles flow abreast with the chamber walls. For example, in some embodiments, the chamber may be configured with a width between approximately 10 microns and approximately 1200 microns. In addition, the device may include one or more light sources adapted to provide incident light through the chamber and a photometer configured to measure the intensity of light transmitted through individual microparticles. In this manner, the chamber may include two opposing view ports through which the incident light may be transmitted. In cases in which the device includes more than one light source, the device may be configured to provide incident light through the chamber at different wavelengths. In addition to the light sources and photometer, the device may include an imaging system configured to acquire images of the flowing fluid within the chamber. In some cases, the device may include a moveable mirror system configured to reflect the light transmitted through the chamber to the imaging system. In addition or alternatively, the imaging system may include a magnification lens configured to enlarge the appearance of individual microparticles within the flowing fluid to be equal to or slightly larger than a pixel size of the images produced by the imaging system. In any case, the device may be a component of a larger system, such as a microencapsulation apparatus, or may be an independent unit.

In some cases, the microparticle analytical device may further include a microprocessor controller with a storage medium having program instructions executable using a processor for analyzing the measured light intensities and acquiring images of the flowing fluid. In particular, the storage medium may include program instructions for identifying and characterizing microparticles within the fluid and determining a quantity of the microparticles. For example, in some embodiments, the storage medium may include program instructions for distinguishing different types of microcapsules contained within the fluid. In addition, the storage medium may include program instructions for distinguishing the microcapsules from debris microparticles. In yet other embodiments, the storage medium may additionally or alternatively include program instructions for determining a shape and size of the microparticles and/or tracking the trajectory of the microparticles within the fluid. In any case, the program instructions used to accomplish such tasks may include instructions for comparing measured intensities of light transmitted through the microparticles at different locations within the chamber. In addition or alternatively, the program instructions may include commands for matching the measured light intensities with spectral characteristics of known microparticles.

A method for identifying and tracking microparticles in motion is also contemplated herein. In particular, the method may include flowing a fluid comprising microparticles in laminar motion through a chamber and transmitting light through the fluid within the chamber and measuring the intensities of the light transmitted through a microparticle. In some embodiments, the step of transmitting light may include transmitting a spectrum of light through the fluid. In any case, the method may further include imaging the fluid a plurality of times as the microparticle flows through the chamber and comparing at least some of the intensities of light between different images of the fluid. In general, the step of comparing the intensities of light may be used to identify and count the microparticles within the fluid. In some embodiments, the step of comparing the intensities of light may be specifically used to calculate a time of flight of individual microparticles and determine trajectories for the individual microparticles.

There may be several advantages to using the microparticle analytical system and method provided herein. For example, the microparticle analytical system offers a manner in which to accurately identify, characterize, track and count microparticles within a flowing fluid. Microparticle size, shape, content and number can be used for feedback control purposes. For instance, the microparticle information obtained from the system and method described herein may be used to optimize the production of microcapsules from a microencapsulation system. In some embodiments, the microparticle analytical device may be portable and, therefore, may be used in a variety of applications, including those in remote regions without power sources. In other embodiments, the analysis system may be included within a microencapsulation system such that the production and processing of microcapsules may be continuous. Such a continuous process averts the disadvantages of down-time and increased production costs associated with batch processing.

BRIEF DESCRIPTION OF THE DRAWINGS

Other objects and advantages of the invention will become apparent upon reading the following detailed description and upon reference to the accompanying drawings in which.

Figure 1:
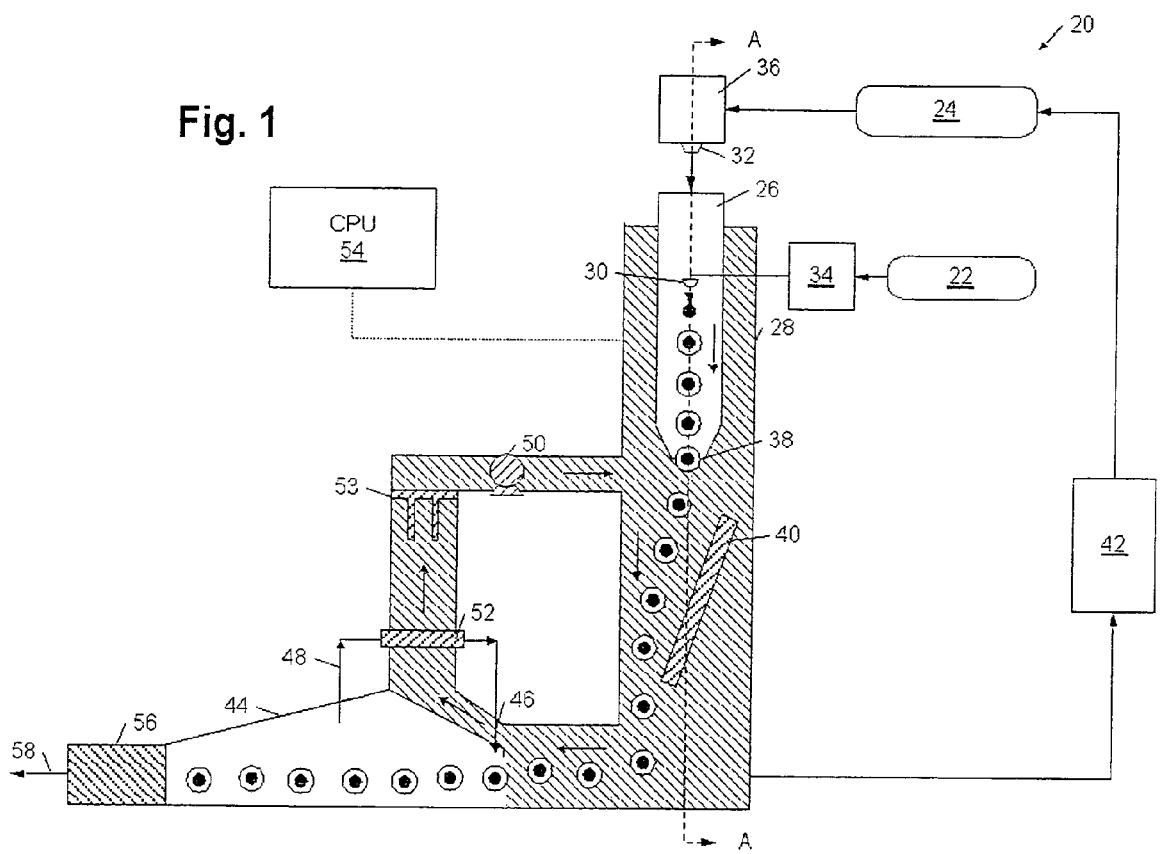
FIG. 1 depicts a schematic diagram of a microencapsulation system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Figure 4:
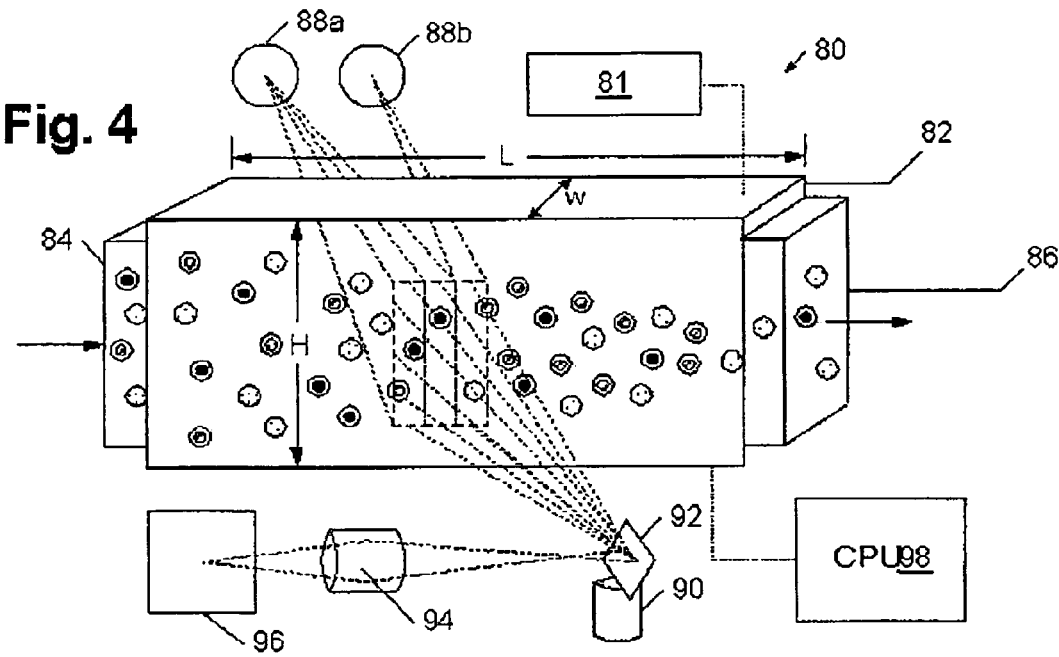
FIG. 4 depicts a schematic diagram of a system configured to analyze microparticles within a flowing fluid.
Figure 5:
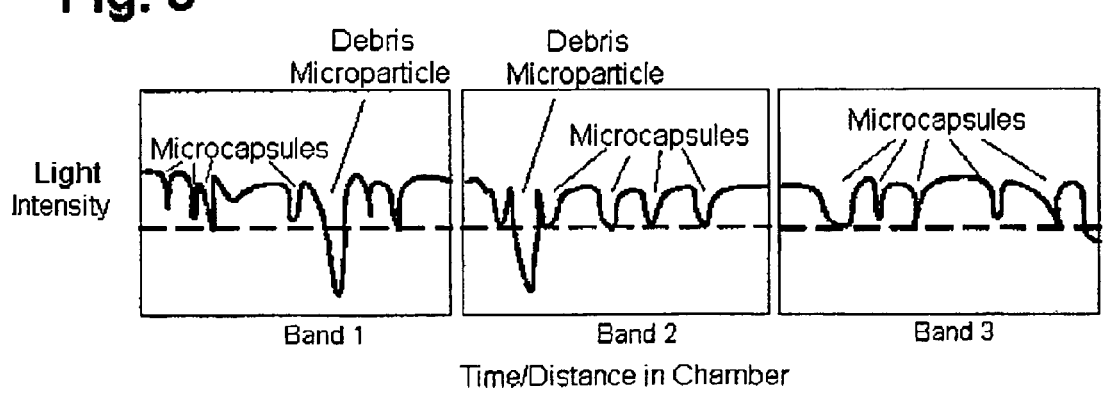
FIG. 5 depicts exemplary graphical data which may be obtained from the microparticle analysis system depicted in FIG. 4.
Figure 6:
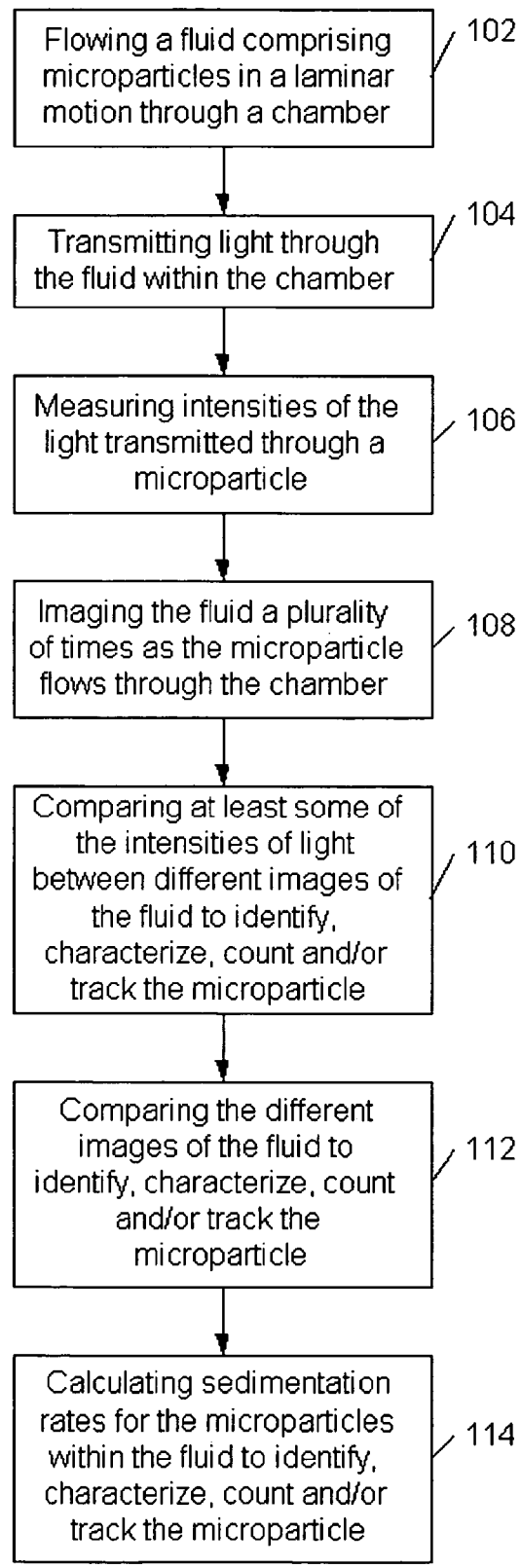
FIG. 6 depicts a flowchart of a method for analyzing microparticles within a flowing fluid.

Turning now to the drawings, exemplary embodiments of a system and a method configured to analyze microcapsules are shown and described in reference to FIGS. 4-6. In particular, FIG. 4 illustrates system 80 configured to track, count, characterize and/or identify microparticles in a flowing fluid. FIG. 5 illustrates exemplary graphical data which may be obtained from system 80 and FIG. 6 depicts a flowchart outlining a method for identifying, counting, characterizing and tracking microparticles in motion. It is noted that although system 80 in FIG. 4, the graphical data in FIG. 5 and the flowchart in FIG. 6 may be used in reference to systems and methods for analyzing microcapsules, such as those fabricated and processed within microencapsulation system 20 of FIG. 1, system 80 and the method depicted in FIG. 6 is not restricted to such an application. In particular, the system and method described in reference to FIGS. 4-6 may be used in a variety of applications in which it may be desirable to track, count, characterize and/or identify microparticles, such as in pharmaceutical and medical applications, waste water processing, bulk pumping of industrial chemicals and ownership identification of liquid products. In addition, the system and method described in reference to FIGS. 4-6 is not restricted to tracking, counting, characterizing and/or identifying microcapsules, but rather may be more broadly used for tracking, counting, characterizing and/or identifying microparticles. As noted above, a "microparticle", as used herein, may include intentionally and unintentionally formed synthetic and naturally occurring particles. In contrast, however, a "microcapsule" may solely refer to synthetically fabricated microspheres. Consequently, the term "microparticle" may encompass a broader range of microspheres.

In general, system 80 may be configured to analyze discrete samples of a stream or an entirety of the stream. In either case, system 80 may be configured to make real-time measurements of microparticles flowing in a pipeline or other flowing liquid system. Consequently, chamber 82 of system 80 may, in some embodiments, be a segment of a chamber or a pipe. In other embodiments, however, chamber 82 may be a distinct component for sampling a fluid from a different chamber. Although FIG. 4 illustrates chamber 82 arranged to induce a horizontal flow of fluid, chamber 82 may alternatively be configured to induce a vertical flow of fluid or any flow other than a horizontal flow. In addition, the system described in reference to FIG. 4 may, in some embodiments, be a portable unit. More specifically, system 80 may be configured such that it can be moved to different locations. In some cases, system 80 may be configured to operate upon battery power. Consequently, in such an embodiment, system 80 may be used in areas in which alternating current (AC) power is not available. Furthermore, system 80 may, in some embodiments, include means 81 configured to flush out chamber 82 such that residual particles may be removed and the chamber can be cleaned. In general, means 81 may be coupled to chamber 82 in a variety of manners. To simplify the illustration of system 80, however, means 81 is shown coupled to system 80 by a dotted line to show a general connection to chamber 82.

As shown in FIG. 4, system 80 may include chamber 82 comprising inlet 84 and outlet 86 with which to respectively introduce and dispense a flowing fluid comprising microparticles. In general, chamber 82 may be configured such that the fluid carries each suspended microparticle abreast with the chamber walls such that each microparticle within the fluid may be detected and tracked individually. In this manner, chamber 82 may be configured to induce a parabolic flow from inlet 84 to outlet 86. In other words, chamber 82 may be configured to induce a drag force within the chamber such that fluid near the center flows at a faster rate than the fluid along the sidewalls of the chamber. In this manner, microparticles within the fluid may change their positions relative to each other as they pass through chamber 82. Consequently, all microparticles within chamber 82 may be accounted for when sequential images of the fluid are taken. The process of obtaining and analyzing the sequential images to identify, track and count microparticles within a fluid is described in more detail below in reference to detector 96.

In a preferred embodiment, system 80 may be configured to induce a laminar flow of fluid through chamber 82. For example, system 80 may be configured to control the flow rate of fluid through chamber 82 (i.e., from inlet 84 to outlet 86) to induce a laminar flow. Although laminar motion of a fluid is dependent on a number of variables, as described below, an exemplary range for system 80 to be adapted to control the flow rate of a fluid may be between approximately 0.10 ml/min and approximately 1.00 ml/min or, more specifically, between approximately 0.10 ml/min and approximately 0.50 ml/min. In some cases, system 80 may be configured to control a flow rate of the fluid through chamber 82 to be between approximately 0.10 ml/min and approximately 0.30 ml/min. Larger or smaller fluid flow rates may be appropriate, however, depending on the design specifications of the system and the fluid in which the microcapsules are immersed. In addition to controlling the flow rate of the fluid to generate a laminar flow, chamber 82 may be configured to generate a laminar flow of fluid in other manners. For example, chamber 82 may be configured to induce a drag force along the chamber walls of chamber 82 which generates a laminar flow of fluid. In addition or alternatively, inlet 84 and/or outlet 86 may be configured to generate a laminar flow of fluid through chamber 82. In particular, inlet 84 and/or outlet 86 may be configured with an opening having dimensions that are substantially similar to height H and width W of chamber 82.

In some cases, the dimensions (i.e., height H, length L and/or width W) of chamber 82 may be configured to generate a laminar flow. Although specific dimensions for height H, length L and width W may be dependent on the design specifications for system 80 and the fluid for which it is configured to allow flow therethrough, an exemplary range for height H may be between approximately 10 microns and approximately 2000 microns, or more specifically between approximately 50 microns and approximately 1000 microns. In addition, an exemplary range for length L may be between approximately 100 microns and approximately 10,000 microns, or more specifically between approximately 100 microns and approximately 5000 microns. Furthermore, an exemplary range for width W may be between approximately 10 microns and approximately 1200 microns or, more specifically, between approximately 10 microns and approximately 100 microns and, in some cases, approximately 20 microns. Larger and/or smaller chamber heights, lengths, and widths of chamber 82, however, may be appropriate. For example, in some embodiments, chamber 82 may be configured to have a width which is approximately 30% to approximately 100% larger than the diameter of the largest microparticle likely to flow through the chamber.

In addition to inducing the fluid in a laminar flow, system 80 may be configured to induce a low shear force within the fluid such that the microparticles are not torn apart. In particular, system 80 may be configured to induce a fluid shear force of less than approximately 100 dynes/cm$^2$ or, more specifically less than approximately 20.5 dynes/cm$^2$. In some cases, it may be advantageous to induce a fluid shear force less than approximately 12 dynes/cm$^2$. In any case, the adaptation of system 80 to control the flow rate and motion of the fluid through chamber 82 may be through the inclusion of flow rate generators or solenoid valves on inlet 84 and/or outlet 86. As described in more detail below, system 80 may, in some embodiments, include CPU 98 with which to operate the flow rate generators and/or solenoid valves.

FIG. 4 further illustrates system 80 having light sources 88a and 88b which are adapted to provide incident light to chamber 82. As shown in FIG. 4, the light from light sources 88a and 88b may, in some embodiments, be transmitted through chamber 82 via the sidewalls of the chamber. Accordingly, the back and front sidewalls of chamber 82, as depicted in FIG. 4, may be translucent. In other cases, light from light sources 88a and 88b may be additionally or alternatively transmitted through chamber 82 via the upper and lower walls of the chamber. In such embodiments, the upper and lower walls of chamber 82 may be translucent. In any case, system 80 provides opposing optical view ports with which to allow incident light from light sources 88a and 88b to transfer through chamber 82.

In some cases, it may be advantageous to transmit light through a relatively small dimension of chamber 82 such that system 80 is allowed to accurately track, count, characterize and identify microparticles within the fluid passing there through. In particular, transmitting light through a relatively narrow dimension of chamber 82 may allow relatively small amounts of the fluid and suspended particles to be analyzed. As a result, a relatively small number of microparticles may exist at a particular section of chamber 82 at a given point in time. More specifically, the density of microparticles in chamber 82 may be such that a substantial number of microparticles are not traversing in the shadow of other microparticles hindering the tracking, counting, characterization and identification of individual microparticles. It is noted that the dimensions of chamber 82 do not necessarily restrict microparticles from traversing in the shadow of each other entirely, but merely serves to minimize the overlap of the number of microparticles in the fluid. As noted above, width W (i.e., the distance between the opposing view ports within the back and front sidewalls of chamber 82) may, in some embodiments, be configured to be the smallest dimension of chamber 82. In particular, chamber 82 may have a width between approximately 10 microns and approximately 200 microns or, more specifically, between approximately 50 microns and approximately 100 microns. In yet other embodiments, height H may be configured to be the smallest dimension of chamber 82, particularly when light sources 88a and 88b are configured to transmit light through the upper and lower walls of the chamber.

In some cases, light sources 88a and 88b may be configured to provide light of different wavelengths. In this manner, intensity measurements of transmitted light, as described in more detail below, may be obtained for a plurality of wavelengths, providing additional data with which to track, count, characterize and identify microparticles. In other words, system 80 may serve as a spectrophotometer by measuring the amount of wavelength-specific, transmitted or reflected light from each microparticle. In some embodiments, one or both of light sources 88a and 88b may be individually configured to provide different wavelengths of light. In such a case, CPU 98 may, in some embodiments, be used to control the selection of wavelengths transmitted from the light sources as described in more detail below. In yet other embodiments, light sources 88a and/or 88b may be configured to provide a single wavelength of light. In any case, system 80 may have any number of light sources, including a single light source or more than two light sources and, therefore, is not restricted to the embodiment depicted in FIG. 4. In cases in which multiple wavelengths of light are transmitted through chamber 82, system 80 may, in some embodiments, include bandpass filters for simultaneous acquisition of the images produced from the transmitted light. Such bandpass filters may be incorporated within detector 96 and/or magnification lens(es) 94, which are described in more detail below. In other embodiments, the band filters may be distinct components from detector 96 and magnification lens(es) 94.

In general, system 80 may be adapted to track, count, characterize and/or identify individual microparticles by obtaining multiple images of the fluid as it traverses through chamber 82 and measuring the intensities of light transmitted through the microparticles as they correspond to the respective images. As such, system 80 may include a photometer configured to measure the intensity of light transmitted through individual microparticles from light sources 88a and 88b. In addition, system 80 may include an imaging system configured to acquire images of the flowing fluid within chamber 82, such as a charge-coupled device (CCD) imaging system. Such a photometer and imaging system are collectively illustrated in FIG. 4 as detector 96. In general, detector 96 may either represent the photometer and imaging system of system 80 as separate components or as integrated components of the same device, depending on the design specifications of the system. A more detailed description of how system 80 is adapted to track, count, characterize and/or identify individual microparticles through the use of detector 96 is described in more detail below in reference to FIG. 5.

As shown in FIG. 4, system 80 may sometimes include moveable mirror 92 to reflect the light transmitted through chamber 82 to detector 96. In general, moveable mirror 92 may be powered by motor 90. In some embodiments, however, moveable mirror 92 may be omitted from system 80. In such an embodiment, detector 96 and light sources 88a and 88b are preferably positioned in alignment with each other. In some cases, detector 96 and light sources 88a and 88b may be configured to move along the length of chamber 82, regardless of whether moveable mirror 92 is included within system 80. In any embodiment, the aforementioned adaptations of system 80 may allow detector 96 to capture sequential images of the fluid as it traverses through chamber 82. In cases in which different wavelengths of light are transmitted through chamber 82, system 80 may be adapted to allow detector 96 to capture images of the same microparticles at each of the multiple wavelengths. Consequently, a multi-spectral absorption data may be obtained for individual microparticles.

An exemplary illustration of wavelength-specific light absorption data depicting microparticles measured in sequential images captured by an imaging system is illustrated in FIG. 5. In particular, FIG. 5 illustrates the intensity of light transmitted through a region of a chamber in which microparticles exist. A narrow range of light transmissions at specific wavelengths may be used to characterize the content of microparticles and, therefore, may be used to identify specific microparticles (i.e., distinguish microcapsules from debris particles and bubbles). As shown in FIG. 5, relatively low transmissions (i.e., high absorptions) of light may be indicative of debris microparticles or bubbles, while relatively high transmissions (i.e., low absorptions) of light may be indicative of microcapsules. In some cases, debris microparticles and/or bubbles may additionally or alternatively exhibit higher transmissions of light than the microcapsules. In any case, the reflection and/or transmission of light from microcapsules may be distinguishable from the reflection and/or transmission of light from debris microparticles and/or bubbles and, therefore, may offer a characteristic with which to track, count, characterize and/or identify microparticles within a fluid as discussed in more detail below. In some embodiments, the reflection of light from the microparticles may be plotted versus time and/or distance within the chamber to further enhance the ability to track, count, characterize and/or identify microparticles within a fluid.

As shown in FIG. 4, system 80 may, in some embodiments, include magnification lens(es) 94 with which to magnify the image acquired by the imaging system of detector 96. In particular, magnification len(es) 94 may be interposed between detector 96 and mirror 92. In yet other embodiments, however, the imaging system of detector 96 may have a magnification lens(es) incorporated therein. In such an embodiment, magnification lens(es) 94 may be omitted from system 80. In either case, magnification lens(es) 94 may, in some embodiments, include a plurality of lenses arranged in series. In other cases, magnification lens(es) 94 may include a plurality of lenses arranged parallel to one another. In such an embodiment, the image reflected from mirror 92 may shine through a plurality of different lenses such that different magnifications of the image may be obtained and analyzed. In yet other embodiments, magnification lens(es) 94 may include a single magnification lens.

In any case, the magnification lens(es) used to enlarge the imaged area of the fluid may include any magnification power which is able to provide an image in which microparticles are clearly visible. For example, the magnification lens(es) may, in some embodiments, include a magnification power which is able to enlarge the appearance of an individual microparticle to be at least the size of one pixel of an image produced by the imaging system of dectector 96. Accordingly, the magnification power of the magnification lens(es) used to enlarge the imaged area of the fluid may generally depend on the size of the microparticles, the area of the fluid to be imaged as well as the design specifications of system 80. Exemplary magnification powers, however, may generally range from approximately 2× to approximately 100× or, or more specifically, between approximately 6× and 75×. In some embodiments, a magnification power of approximately 45× has been found to provide sufficient magnification such that the microcapsules may be easily visualized on a computer monitor.

As noted above, system 80 may be configured to compare light intensity measurements of consecutive images of the fluid such that individual microparticles may be tracked, counted, characterized and/or identified. More specifically, system 80 may be configured to coordinate the images from the imaging system of detector 96 with the light intensities measured by the photometer of detector 96 such that the size, shape, and/or types of microparticles within the fluid may be identified, characterized and counted. In general, debris microparticles and bubbles may vary in size and shape and, therefore, may have similar shapes and sizes as microcapsules in some embodiments. As noted above, however, debris microparticles and bubbles do not absorb the same amount of light as microcapsules. As such, based upon the measured light intensities of the particles, system 80 may be used to identify and characterize microparticles. In particular, the coordinated images may aid in distinguishing different types of microcapsules as well as distinguishing microcapsules from other microparticles (e.g., debris or bubbles) within the fluid since microcapsules will be characterized by particular sizes and the amount of light they will absorb or reflect. In this manner, a concentration of the microparticles within the fluid may also be determined using detector 96. In general, the identification of a target microparticle is accomplished by comparing the transmitted light received on an adjacent pixel and then subtracting the light level recorded for the target microparticle as it passes from pixel to pixel.

In addition to determining the shape, size and type of microparticles within the fluid, the density of individual microparticles may be determined from the images acquired from the imaging system of detector 96. In particular, the intensity of the transmitted or reflected light from each microparticle may be measured, then select values above a threshold may be recorded according to the pixel location in the captured image array. Time of flight of individual microparticles may be calculated between the images and, consequently, trajectories of the individual microparticles may be determined according to a pre-determined algorithm. The density of the individual microparticles may, in turn, be calculated from the trajectory of the microparticles. In addition, system 80 may be able to distinguish microcapsules from buoyant or sedimenting non-microcapsules by tracking the trajectory of the microparticles. In any case, the adaptation of system 80 to synchronize images from the imaging system with the light intensities measured by the photometer may be incorporated into detector 96 or may be controlled through CPU 98 as discussed in more detail below.

As shown in FIG. 4, system 80 may include central processing unit (CPU) 98 to control operation of system 80. In particular, system 80 may include a dedicated microprocessor-based controller or a general-purpose computer configured to automate the operations of system 80 such that microparticles may be tracked, counted, characterized and/or identified. Consequently, the method described in reference to FIG. 6 below may, in some embodiments, be a computer-implemented method. As described below, CPU 98 may be used to control a variety of components within system 80 and, accordingly, may be coupled to the components of system 80 which it is configured to control. Such individual connections to the components, however, are not illustrated in FIG. 4 to simplify the illustration of system 80. Instead, CPU 98 is shown coupled to system 80 by a dotted line to show a general connection to the components included within system 80.

In some cases, CPU 98 may be configured to control the operation of light sources 88a and 88b such that the angle, position and/or wavelength of light transmitted to chamber 82 may be regulated. In addition, CPU 98 may be configured to control the movement of moveable mirror 92 in order to capture sequential images of the fluid passing through chamber 82. In some cases, CPU 98 may be used to control the flow rate of the fluid through chamber 82. In addition, CPU 98 may be configured to control detector 96 for capturing images of the fluid within chamber 82 as well as measuring the intensities of light transmitted through the microcapsules. Such operational control adaptations of CPU 98 may be incorporated within a storage medium of CPU 98 having program instructions with which to regulate the operation of system 80 such that microparticles may be tracked, counted, characterized and/or identified in a flowing fluid. In particular, CPU 98 may include program instructions with which to control the operation of light sources 88a and 88b, moveable mirror 92, detector 96 and/or the flow rate of fluid through chamber 82 as described above.

In addition, CPU 98 may include program instructions with which to analyze the measured light intensities from the photometer within detector 96 as well as the images captured from the imaging system within detector 96. More specifically, CPU 98 may include program instructions for identifying microparticles that include comparing measured intensities of light transmitted through the microparticles at different locations within the chamber. In addition, CPU 98 may include program instructions that include matching measured light intensities with spectral characteristics of known microparticles. In this manner, CPU 98 may include program instruction with which to identify, characterize and count microparticles within a flowing fluid as well as track a trajectory of the microparticles through the chamber. More specifically, CPU 98 may include program instructions with which to distinguish different types of microparticles contained within the fluid, such as different types of microcapsules and/or debris microparticles within the fluid. In addition, CPU 98 may include program instructions with which to determine the shape, size and density of microparticles within the fluid. In some embodiments, CPU 98 may be adapted to identify, characterize, track and count more than 1000 microparticles at a time. In addition, CPU 98 may be adapted to identify, characterize and track a microcapsule in approximately 5 seconds or less.

FIG. 6 illustrates a flowchart of a method for analyzing microparticles within a flowing fluid. As shown respectively in steps 102 and 104 of FIG. 6, the method may include flowing a fluid comprising microparticles in a laminar motion through a chamber and transmitting light through the fluid within the chamber. An exemplary explanation of such process steps are described above in reference to FIG. 4 in which a fluid is respectively introduced and dispensed from inlet 84 and outlet 86 and light sources 88a and 88b are used to transmit light through chamber 82. In particular, the step of flowing the fluid in a laminar motion may involve controlling the flow rate of the fluid through chamber 82 and/or configuring chamber 82 to generate a laminar flow of fluid. In particular, chamber 82 may be configured such that the drag force along the sidewalls of the chamber to generate a laminar flow of fluid. In addition or alternatively, inlet 84, outlet 86 and/or chamber 82 as a whole may be configured with dimensions to generate a laminar flow of fluid. In any case, the step of transmitting the light through the fluid may involve transmitting a single wavelength of light or a spectrum of light through the fluid.

As noted in step 106, the method may further include measuring the intensities of the light transmitted through a microparticle. Such light intensity measurements may be conducted by a photometer of the system as described in more detail above in reference to detector 96. As shown in FIG. 6, the method may further include step 108 in which the fluid is imaged a plurality of times as the microparticle flows through the chamber. Such an imaging process is described above in reference to detector 96 as well. Step 110 notes that at least some of the measured intensities of light between the different images of the fluid may be compared. In addition, step 112 outlines that the different images may be compared. Although step 110 is shown prior to the step of 112, step 112 may alternatively be conducted prior to or at substantially the same time as step 110.

In any case, the comparisons may generally be used to identify, characterize and/or count the microparticles within the fluid as described above in reference to system 80 in FIG. 4. In addition or alternatively, the comparisons may be used to track the microparticles within the fluid. For example, in some embodiments, the comparisons of the different images may be used to calculate a time of flight and trajectories of individual microparticles. In some cases, the density of the individual microparticles may be calculated from the trajectories. In yet other cases, the density of the individual microparticles may be determined by terminating the flow of the fluid within the chamber and calculating buoyancy and/or sedimentation rates for the microparticles within the fluid. In other embodiments, the flow of the fluid may not need to be terminated in order to calculate the buoyancy and/or sedimentation rates of the microparticles. In either case, the calculation of trajectories, or more specifically buoyancy and/or sedimentation rates of the microparticles, may also be used to identify and distinguish different types of microparticles within the fluid as noted in step 114. For example, step 114 may be used to distinguish microcapsules from debris microparticles or bubbles. Such a distinction, however, may also or alternatively be determined by comparing the measured light intensities and/or images of the fluid as described in reference to steps 110 and 112.

As noted above, the system and method described in reference to FIGS. 4-6 may be used to analyze and characterize any type of microparticles, including those which are produced naturally and those which are synthetically produced. In addition, the analytical system described above may be incorporated for any application in which microparticles are suspended within a fluid. For example, the microparticle analytical system may be used in pharmaceutical and medical applications, waste water processing, bulk pumping of industrial chemicals and ownership identification of liquid products. In some cases, the system and method for analyzing and characterizing microparticles may be used during the fabrication of microparticles. In particular, the system and method described above may, in some embodiments, be used to monitor the production of microparticles to insure the microparticles are formed within design specifications. An exemplary embodiment of a microcapsule production unit which may include the microparticle analytical system described herein is discussed in detail below in reference to FIGS. 1-3. The description of such a production unit is provided to illustrate an exemplary embodiment in which the microparticle analytical system described above may be used. It is noted, however, that the use of the microparticle analytical system is not restricted to the production of microcapsules. In particular, the microparticle analytical system described may be used for any application in which microparticles are suspended within a fluid. Consequently, the system and method described herein may be used to analyze and characterize microparticles independent of a production unit.

Figure 2:
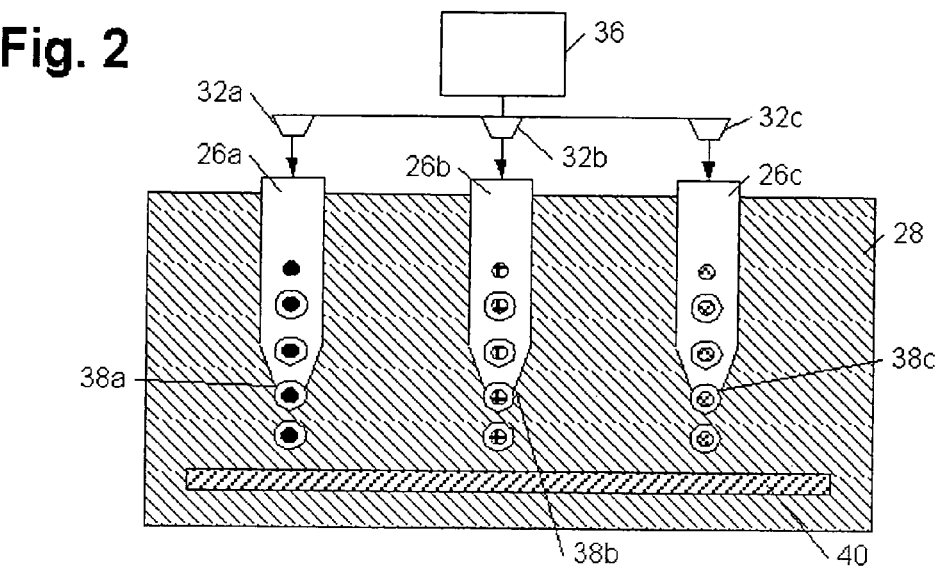
FIG. 2 depicts a partial cross-sectional view of the microencapsulation system depicted in FIG. 1.
Figure 3:
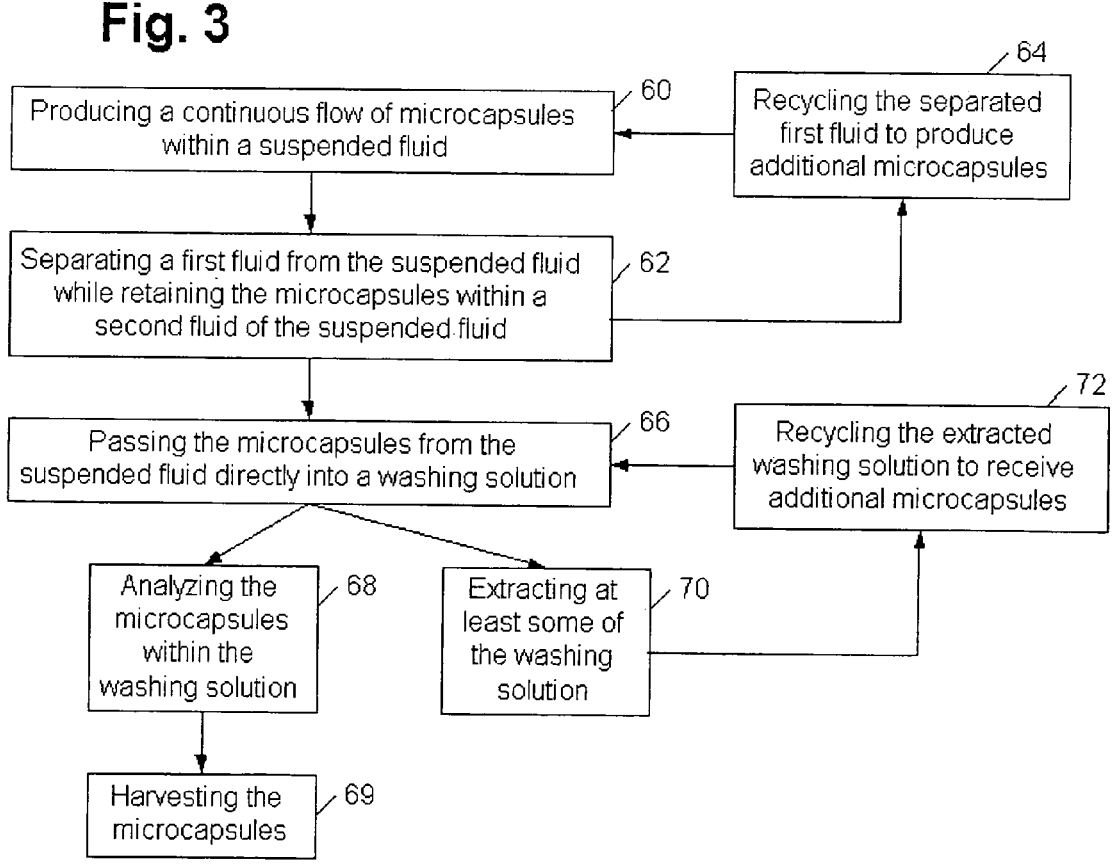
FIG. 3 depicts a flowchart of a method for producing and processing microcapsules.

As noted above, exemplary embodiments of a system and a method for fabricating synthetic microcapsules are shown in FIGS. 1-3. In particular, FIG. 1 illustrates a schematic view of microencapsulation system 20 and FIG. 3 illustrates a flowchart outlining a method for producing microcapsules using such a system. FIG. 2 illustrates a partial cross-sectional view of microencapsulation system 20 taken along line AA of FIG. 1. In general, microencapsulation system 20 may be adapted to encapsulate liquid and/or solid particles and process the microcapsules in a single continuous system. More specifically, microencapsulation system 20 may be adapted to produce, cure, wash and analyze a continuous flow of microcapsules without disrupting the production flow of the microcapsules. In some embodiments, microencapsulation system 20 may include additional mechanisms with which to process microcapsules. Such mechanisms may be those known for use in the industry of microencapsulation and incorporated within microencapsulation system 20 in a manner accommodating a knowledgeable sequence of process steps. As described in more detail below, the fabrication and processing of microcapsules employs a variety of fluids. In an effort to simplify the drawings, however, the illustrations of microencapsulation system 20 in FIGS. 1 and 2 do not depict the presence of such fluids within the system with exception to the formation of the microcapsules. Instead, the different components of microencapsulation system 20 are distinguished by reference numbers and, in some cases, accompanying cross-hatch patterns.

As shown in FIG. 1, microencapsulation system 20 may include reservoirs 22 and 24, inner chamber 26, chamber 28 and microsphere dispensers 30 and 32, all of which may constitute a "microcapsule production unit" of microencapsulation system 20. In particular, reservoirs 22 and 24, inner chamber 26, chamber 28 and microsphere dispensers 30 and 32 may be collectively adapted to form microcapsules having one or more encapsulated particles and/or fluids. In some embodiments, microencapsulation system 20 may include pulsatile flow generators 34 and 36 respectively coupled to reservoirs 22 and 24 as shown in FIG. 1. In such embodiments, pulsatile flow generators 34 and 36 may be constitute a part of the microcapsule production unit of microencapsulation system 20. As discussed in more detail below, however, pulsatile flow generators 34 and 36 are not necessarily needed for the generation of microcapsules in some embodiments. Consequently, one or both of pulsatile flow generators 34 and 36 may be omitted from microencapsulation system 20 in some embodiments. As noted above, a "microcapsule", as used herein, may generally refer to a droplet of material synthetically encased with an outer protective shell having a diameter ranging from sub-micron dimensions to a few hundred microns. Such a term may generally be synonymous with any spherical microscopic vesicle including microspheres, micelles, inverted micelles, bilayer vesicles and lipsomes.

The microcapsules described herein and fabricated using microencapsulation system 20 are generally directed at microspheres having a dual-material inner core encapsulated by a polymer membrane. In particular, the processing of microcapsules described in more detail below is generally directed toward microcapsules having an inner core of one material surrounded by an intermediate shell of an immiscible material, which is in turn surrounded by an outer polymer shell. The system and method described herein, however, are not restricted to fabricating microcapsules with such structure. In particular, the system and method described herein may be used to form and process microcapsules having any number and arrangement of materials encapsulated by an outer membrane, including microcapsules with a single inner material and others with more than two inner materials encapsulated by an outer membrane.

In general, reservoirs 22 and 24 may be adapted to store materials with which to form the interior of a microcapsule. In some medical or pharmaceutical applications, reservoir 22 may be specifically configured to store a contrast agent medium for imaging CT scans, while reservoir 24 may be configured to store an aqueous drug solution, such as antibiotics, enzymes and/or immune stimulants. In other cases, reservoir 22 may be adapted to store live cells for transplantation purposes and reservoir 24 may be adapted to store an immunosuppressant medium. In such an embodiments, the fluid stored within reservoir 22 may be configured to serve as a drug carrier within the interior of a microcapsule. Other mediums used in the medical or pharmaceutical industry may also or alternatively be stored within reservoirs 22 and 24. In yet other embodiments, materials which are used to form microcapsules for applications other than for the pharmaceutical and medical industries may be stored within reservoirs 22 and 24. In particular, reservoirs 22 and 24 may be used to store mediums which are known to be used for the production of microcapsules in applications for waste water processing, bulk pumping of industrial chemicals and/or ownership identification of liquid products.

In any case, reservoirs 22 and 24 are preferably used to store materials which are immiscible to each other such that the materials do not become a homogeneous mixture upon formation of the microcapsule. For example, in some embodiments, reservoirs 22 and 24 may be used to store materials with which to respectively form an inner core and an intermediate shell of a microcapsule as described above. The term "immiscible", as used herein, may generally refer the solubility of multiple materials having no more than 10 gm/100 ml in an adjoining material and that the adjoining materials form an interface resembling a meniscus. In other embodiments, however, materials which form a homogenous mixture may be respectively stored within reservoirs 22 and 24.

As noted above, microencapsulation system 20 may, in some embodiments, be configured to encapsulate more than two materials. For example, in some cases, reservoirs 22 and/or 24 may be adapted to store more than one material such that the inner core and/or the intermediate shell of a microcapsule may each include more than one medium. More specifically, reservoirs 22 and/or 24 may include a plurality of reservoirs and/or may be configured to have different compartments such that a variety of materials may be stored within the reservoirs. Consequently, reservoirs 22 and 24, as used herein, may respectively represent a single reservoir or multiple reservoirs. In some embodiments, microencapsulation system 20 may be configured to encapsulate a single material. As such, in some embodiments, one of reservoirs 22 and 24 may be omitted from microencapsulation system 20. In yet other embodiments, however, microencapsulation system 20 may be adapted to separately encapsulate the materials stored within reservoirs 22 and 24. In this manner, microencapsulation system 20 may be adapted to form different types of microcapsules, each with a different single-material interior. In some cases, microencapsulation system 20 may be additionally or alternatively adapted to form different types of microcapsules with multi-material interiors.

In any case, microencapsulation system 20 may be configured to allow a variety of different microcapsules, particularly microcapsules having different viscosities, to be formed within a single system. An exemplary embodiment of microencapsulation system 20 including an adaptation to form a variety of different microcapsules is illustrated in FIG. 2 and described in more detail below. It is noted that the variety of microcapsules which may be formed from a microencapsulation system having such an adaptation may differ not only by composition, but also or alternatively by the number of materials within the microcapsule and/or the structure of the microcapsule. In general, the "structure" of a microcapsule, as used herein, may generally refer to the arrangement of materials within the microcapsule. For example, one structure of a microcapsule may include an inner core of one material surrounded by an intermediate shell of an immiscible material, which is in turn surrounded by an outer polymer shell. An alternative microcapsule structure may include two immiscible materials forming two halves of a spherical droplet which is in turn surrounded by an outer polymer shell. Other microcapsule structures may be formed as well using the system and method described herein, depending on the design specifications of the system and microcapsule to be formed.

As shown in FIG. 1, microencapsulation system 20 may, in some embodiments, be adapted to introduce the materials stored within reservoirs 22 and 24 into inner chamber 26 of chamber 28. More specifically, microencapsulation system 20 may include microsphere dispensers 30 and 32 which are adapted to respectively discharge material stored within reservoirs 22 and 24 into inner chamber 26. In general, the volume ratio of materials respectively discharged from reservoirs 22 and 24 to form the interior of a microcapsule may be between approximately 1:2 and approximately 1:10 or, more specifically, between approximately 1:5 and approximately 1:10. In embodiments in which reservoir 24 stores an aqueous drug solution, it may be particularly advantageous to employ volume ratios between approximately 1:5 and approximately 1:10 to maximize the drug payload of the microcapsule. In some embodiments, particulate matter may be combined with the materials from reservoirs 22 and 24 to form the interior of a microcapsule. In such an embodiment, the volume ratio of the particulate matter may be less than approximately 1% of the total volume of the microcapsule interior.

In some embodiments, the ratio of materials used to form the interior of a microcapsule may be characterized with regard to the density of the materials rather than the volume of materials. In particular, the density of materials respectively discharged from reservoirs 22 and 24 to form the interior of a microcapsule may be between approximately 1:2 and approximately 1:10 or, more specifically, between approximately 1:5 and approximately 1:10. In any case, the volume and density ratios of materials forming an interior of a microcapsule may vary, depending on the design specifications and intended application of the microcapsules. Consequently, smaller or larger volume and/or density ratios than the ones recited above may be appropriate.

As noted above, microencapsulation system 20 may, in some embodiments, be configured to form microcapsules having an inner core of one material surrounded by an intermediate shell of an immiscible material, which is in turn surrounded by an outer polymer shell. As such, in some cases, microencapsulation system 20 may be configured to dispense materials from microsphere dispensers 30 and 32 such that the material discharged from reservoir 24 may coat the material discharged from reservoir 22. In particular, microsphere dispenser 32 may, in some embodiments, be configured to fill inner chamber 26 such that droplets of the material from reservoir 22 may be dispensed into a bath of the material from reservoir 24. In other embodiments, microsphere dispenser 32 may be configured to dispense just enough material into inner chamber 26 to envelop a single droplet of material dispensed from microsphere 30 for the formation of each microcapsule.

In either case, microsphere dispensers 30 and 32 may be arranged in alignment with each other. "Arranged in alignment", as used herein, may generally refer to the placement of microsphere dispensers 30 and 32 relative to each other to dispense materials from reservoirs 22 and 24 such that spherical droplets comprising the two materials may be formed. In other words, microsphere dispensers 30 and 32 may be arranged such that the material from reservoir 24 encases a droplet of material from reservoir 22. In some embodiments, microsphere dispenser 32 may be arranged above microsphere dispenser 30 as shown in FIG. 1. In other embodiments, microsphere dispenser 32 may be arranged in the vicinity of microsphere dispenser 30 or, more specifically, at approximately the same location as microsphere dispenser 30. In yet other cases, microsphere dispensers 30 and/or 32 may be positioned near opening 38 of inner chamber 26. In general, opening 38 may serve as an orifice or nozzle by which to pass spherical droplets formed of the materials from reservoirs 22 and 24 into chamber 28. In this manner, the spherical droplets, in some embodiments, may be formed upon passing through opening 38.

In general, the viscosity and surface properties of the materials used to form the spherical droplets may influence the distance at which to position microsphere dispensers 30 and 32 as well as the frequency and flow rate at which to discharge materials from reservoirs 22 and 24 such that the spherical interiors of the microcapsules may be formed. As such, microsphere dispensers 30 and 32 may be spaced farther or closer together than depicted in FIG. 1. An exemplary distance between microsphere dispensers 30 and 32 may generally be less than 1 inch, however, the dispensers may be spaced apart by larger distances in some cases. In some embodiments, microsphere dispenser 32 may be arranged within inner chamber 26, such as near microsphere dispenser 30 and/or opening 38 as noted above. In any case, microsphere dispensers 30 and 32 may be configured to move within microencapsulation system 20 in some embodiments.

In view of the alignment configurations of microsphere dispensers 30 and 32 and opening 38 discussed above, microencapsulation system 20 may be configured to produce a vertical flow of spherical droplets formed from the materials stored within reservoirs 22 and 24. For example, a vertical flow of spherical droplets may, in some embodiments, be formed within inner chamber 26 as shown in FIG. 1. In other cases, a vertical flow of spherical droplets may be formed upon passing through opening 38. In either case, the spherical droplets may be gravity lead through microencapsulation system 20 in addition to or alternative to being lead via a fluid through the system. In other embodiments, however, microencapsulation system 20 may be configured to produce a production flow of spherical droplets other than a vertical production flow. For example, in some cases, microencapsulation system 20 may be configured to produce a production flow spherical droplets which traverse nearly horizontal through the system. In particular, inner chamber 26 and/or chamber 28 may be arranged on its side relative to the illustration shown in FIG. 1. In such a case, microsphere dispensers 30 and 32 may, in some embodiments, be arranged at substantially the same level within microencapsulation system 20. In yet other embodiments, however, microsphere dispensers 30 and 32 may be arranged in vertical alignment with each other. In either case, microsphere dispensers 30 and 32 may be arranged such that the material discharged from reservoir 22 may be encapsulated by the material discharged from reservoir 24.

As noted above, microencapsulation system 20 may be configured to dispense distinct droplets of material from microsphere dispensers 30 and/or 32 in some embodiments. In some cases, microencapsulation system 20 may include pulsatile flow generators 34 and 36 respectively coupled between reservoirs 22 and 24 and microsphere dispensers 30 and 32. Such pulsatile flow generators may be configured to supply materials from reservoirs 22 and 24 at any flow rate and frequency suitable for the generation of microcapsules having a diameter ranging from sub-micron dimensions to hundreds of microns, or more specifically between approximately 1 micron and approximately 800 microns and even more specifically between approximately 1 micron and approximately 300 microns. The nozzles included within microsphere dispensers 30 and 32 and/or opening 38 may be adapted to form microcapsules of such size as well. More specifically, microsphere dispensers 30 and 32 and/or opening 38 and, in some embodiments, pulsatile flow generators 34 and 36 may be configured to dispense the materials form reservoirs 22 and 24 in a synchronous manner to form microcapsules with co-axial interiors. In this manner, spherical droplets having an inner core of material from reservoir 22 and an intermediate shell of material from reservoir 24 may be formed. In some embodiments, pulsatile flow generators 34 and/or 36 and the nozzles within microsphere dispensers 30 and 32 and opening 38 may be configured to generate a flow of materials at an ultrasonic frequency. Microencapsulation system 20 may be configured to deliver materials at lower or higher frequencies, however, depending on the design specifications of the system.

As noted above, one or both of pulsatile flow generators 34 and 36 may be omitted from microencapsulation system 20 in some embodiments. Consequently, the generation of microcapsules within microencapsulation system 20 may not be dependent on the inclusion of such flow generators. In particular, microencapsulation system 20 may be configured to generate microcapsules with the aforementioned diameters using other means, such as the inclusion of one or more pulsatile pumps coupled to microsphere dispensers 30 and 32 and/or opening 38. In yet other embodiments, microsphere dispensers 30 and 32 and/or opening 38 may be spaced apart by a distance sufficient to form microcapsules without the use of pulsatile mechanisms coupled to both dispensers, as described in more detail below.

As noted above, an exemplary embodiment of microencapsulation system 20 configured to form a variety of different microcapsules is shown in FIG. 2. Such an illustration is a cross-sectional view of microencapsulation system 20 taken along line AA of FIG. 1. As shown in FIG. 2, microencapsulation system 20 or, more specifically, inner chamber 26 may, in some embodiments, include a plurality of inner chambers 26a-26c. It is noted that although FIG. 2 illustrates the inclusion of three inner chambers within microencapsulation system 20, microencapsulation system 20 may include any number of inner chambers. In some cases, microencapsulation system 20 may include an array of inner chambers within chamber 28. In any case, although inner chambers 26a-26c are shown uniformly spaced within chamber 28 and include substantially similar dimensions, inner chambers 26a-26c may alternatively be spaced non-uniformly within chamber 28 and/or having different dimensions than each other. In some cases, microencapsulation system 20 may be configured to dispense a different material within each of inner chambers 26a-26c, as illustrated in FIG. 2 by the different cross-hatch patterned droplets. In other embodiments, however, microencapsulation system 20 may be configured to dispense the same material within each of inner chambers 26a-26c. In either case, the materials dispensed into inner chambers 26a-26c may be from reservoirs 22 and 24 as described above in reference to FIG. 1 and, therefore, may be used to form the inner cores of the microcapsules in some embodiments.

FIG. 2 illustrates pulsatile flow generator 36 arranged above inner chambers 26a-26c. As noted above, pulsatile flow generator 36 may be configured to regulate the flow of material from reservoir 24 through microsphere dispenser 32 or, more specifically, through microsphere dispensers 32a-32c as shown in FIG. 2. In yet other embodiments, microencapsulation system 20 may not include pulsatile flow generator 36. In some embodiments, reservoir 24 may include a single type of material and microsphere dispensers 32a-32c, openings 38a-38c and/or pulsatile flow generator 36 may be configured to discharge the material such that the material coats the droplets of material discharged from reservoir 22. In this manner, microencapsulation system 20 may be configured to form microcapsules having inner cores of different materials surrounded by intermediate shells of the same material.

Alternatively, microencapsulation system 20 may, in some embodiments, be configured to form microcapsules having inner cores of the same material surrounded by intermediate shells of different materials. More specifically, microencapsulation system 20 may be configured to discharge the same material from reservoir 22 and different materials from reservoir 24. In yet other embodiments, microcapsulation system 20 may be configured to form microcapsules having a variety of different inner core materials and different intermediate shell materials. In any case, the material within reservoir 22 may be discharged through one or more microsphere dispensers and, in some embodiments, by one or more pulsatile flow generators similar to the manner described in reference to microsphere dispenser 30 and pulsatile flow generator 34 in FIG. 1. Such microsphere dispensers and pulsatile flow generators, however, are not shown in FIG. 2 due to the cross-sectional view of the drawing.

As noted above, microencapsulation system 20 may, in some embodiments, be configured to form microcapsules having structures other than the one described above having an inner core and intermediate shell surrounding such an inner core. Consequently, it is noted that microencapsulation system 20 may be adaptively configured to accommodate different types of microcapsule structures. In addition, although the droplets in FIG. 2 are shown to be substantially uniform in size, microencapsulation system 20 may be adapted to dispense and form droplets of varying sizes. In particular, microencapsulation system 20 may be adapted to dispense and form droplets of different sizes within each of inner chambers 26a-26c. In some embodiments, however, it may be advantageous to form the microcapsules to be substantially uniform in size. For instance, the packing density of the microcapsules may be maximized when they are substantially uniform in size. In other embodiments, it may be advantageous to form the microcapsules to be substantially uniform in size and volume ratio such that amount of fluid within the microcapsules may be substantially uniform. Such a condition may be particularly advantageous in embodiments in which the microcapsules are used for the delivery of drugs.

Returning to FIG. 1, inner chamber 26 is shown nested within an upper portion of chamber 28 and includes opening 38 at the bottom thereof. Consequently, inner chamber 26 may serve as a module to direct spherical droplets into chamber 28 via opening 38. In general, chamber 28 may contain a polymer/solvent solution with which to coat the spherical droplets dispensed from inner chamber 26. As such, the spherical droplets formed within inner chamber 26 may be dispensed directly into the polymer/solvent solution. In general, the polymer/solvent solution forms an immiscible outer membrane around the spherical droplet to form a microcapsule. The formation of the outer membrane is achieved in such a way that minimal shear and mixing occurs between the outer membrane and spherical droplet. More specifically, the two phases are brought together such that the fluid shear properties are controlled to levels not exceeding 150 dynes/cm$^2$, and the adsorptive surface properties at the immiscible interface are not significantly altered. In some embodiments, the fluid shear properties may be controlled to levels below 80 dynes/cm$^2$ or, more specifically, below 12 dynes/cm$^2$. Larger or smaller fluid shear levels may be appropriate, however, depending on the design specifications of microencapsulation system 20.

As noted above, a "microcapsule", as used herein, may generally refer to a droplet of material synthetically encased with an outer protective shell having a diameter ranging from sub-micron dimensions to a few hundred microns. In some embodiments, the polymer/solvent solution may include particles which can be activated by external magnetic or ultrasonic fields, such as one or more ceramic-ferromagnetic particles. Such an inclusion of particles may be particularly advantageous in industry applications in which the microcapsules are later exposed to magnetic or ultrasonic fields. For example, in embodiments in which the microcapsules include aqueous drug solutions or dyes, the trigger particles may be used to time the release of the drug or dye within the microcapsules. More specifically, a microcapsule coated with trigger particles may be configured to remain intact until exposed to magnetic or ultrasonic fields. In this manner, microcapsules may be ingested and travel within a body to a target location before the drug therein is released, allowing more efficient use of the drug. Alternatively, trigger particles may be used to release dyes within a fluid for identification purposes. In yet other embodiments, trigger particles may be used to enhance the identification of the microcapsules within a fluid as described in more detail below.

In addition to coating the spherical droplet formed within inner chamber 26, the polymer/solvent solution may further serve to guide the microcapsules through chamber 28. More specifically, the polymer/solvent solution may serve to suspend the microcapsules such that the rate the microcapsules descend through chamber 28 may be controlled. In a preferred embodiment, the microcapsules may be heavier than the polymer/solvent solution and, therefore, may be transferred through the solution by gravity in some cases. As shown in FIG. 1, the microcapsules moving through chamber 28 may be directed toward separation baffle system 40. Such a separation baffle system may be used to recover the residual materials carried from inner chamber 26 which were not used to form the spherical droplets. In some cases, separation baffle system 40 may also be used to recover the materials from microcapsules which break during the production process. In any case, separation baffle system 40 may be more specifically used to recover materials which are not soluble with the polymer/solvent solution. Such materials may include materials dispensed from reservoirs 22 and/or 24.

As shown in FIG. 1, the recovered material may be routed from chamber 28 to phase separation recovery unit 42. In general, phase separation recovery unit 42 may be used to separate the materials recovered from separation baffle system 40. In embodiments in which the material originally stored within reservoir 24 is separated from the recovered solution, the material may be recycled back to reservoir 24 as shown in FIG. 1. Such an embodiment may be particularly advantageous in embodiments in which an aqueous drug solution is stored within reservoir 24. In particular, the recycle process may reduce consumption of the drug solution within microencapsulation system 20, thereby lowering processing costs, particularly since drug solutions tend to be relatively costly. In other embodiments, the material originally stored within reservoir 22 may additionally or alternatively be separated from the recovered solution and may, in turn, be recycled back to reservoir 22. In yet other embodiments, the materials removed from chamber 28 may be disposed.

In any case, subsequent to passing through separation baffle system 40, the microcapsules are carried through chamber 28 to washing compartment 44. As shown in FIG. 1, a portion of chamber 28 may extend above washing compartment 44. Such a portion of chamber 28 may serve as a side conduit to recover and recycle the polymer/solvent solution used to suspend the microcapsules prior to, during, and subsequent to traversing through separation baffle system 40. More specifically, pump 50 may be used to draw the polymer/solvent solution from the bottom of chamber 28 such that only a small amount of the solution is transported into washing compartment 44. The recovered polymer/solvent solution may be returned to the main compartment of chamber 28 to encapsulate and suspend the spherical droplets produced from inner chamber 26. In some cases, phase separator 53 may be included in the side conduit of chamber 28. In general, phase separator 53 may be used to separate and dispose of residual materials included within the polymer/solvent solution such that the polymer/solvent solution may return to the main compartment of chamber 28 unpolluted. Such residual materials may include but are not limited to the materials used to form the spherical droplets within inner chamber 26 and which were not recovered in separation baffle system 40.

In general, washing compartment 44 may include a fluidized passage for washing and harvesting microcapsules dispensed from the microcapsule production unit of microencapsulation system 20 or, more specifically, from separation baffle system 40. In particular, washing compartment 44 may include a washing solution with which to remove residual polymer/solvent solution from microcapsules transported from chamber 28. In some cases, the washing solution may be used to cure the microcapsules. In particular, the washing solution may include a component by which to strengthen the outer membrane of the microcapsules. As shown in FIG. 1, the washing solution may be introduced into washing compartment 44 through dispenser 46. It is noted that the washing solution may be introduced into washing compartment 44 in other manners as well or alternatively, depending on the design specifications of microencapsulation system 20. In some cases, washing compartment 44 may configured to suspend the microcapsules within a flowing stream of the washing solution. In this manner, the microcapsules may be transported through washing compartment 44 and subsequently harvested at or subsequent to exit 58.

As shown in FIG. 1, microencapsulation system 20 may include recirculation line 48 routed from washing compartment 44 to pass the washing solution through phase separator 52 back to dispenser 46. In some embodiments, recirculation line 48 may be one a plurality of recirculation lines routed from washing compartment 44, each used to withdraw a different density fluid from the compartment. In general, phase separator 52 may be used to separate the polymer/solvent solution rinsed from the microcapsules in washing compartment 44 from the washing solution. In this manner, the washing solution may be returned to washing compartment 44 through dispenser 46 and the polymer/solvent solution may be routed to the side conduit of chamber 28. In some embodiments, phase separator 52 may be also used to separate any other materials recycled from washing compartment 44. For example, residual amounts of the materials used to form the spherical droplets within inner chamber 26 and which were not recovered in separation baffle system 40 may be removed from the recycled stream.

In any case, it may be advantageous, in some embodiments, to have washing compartment 44 configured to allow the polymer/solvent solution and other residual materials to separate from the washing fluid prior recirculating the fluid back through recirculation line 48. In particular, washing compartment may, in some embodiments, be configured to be long enough such that the different density fluids can separate from each other. In such embodiments, recirculation line 48 and any other recirculation lines coupled to washing compartment 44 may be positioned near the end of the washing compartment. In other embodiments, however, microencapsulation system 20 may not include recirculation lines. Instead, the washing solution used to rinse the microcapsules may be disposed upon harvesting the microcapsules.

In addition to having a microcapsule production unit, separation baffle system 40 and washing compartment 44, microencapsulation system 20 may further include means 56 for analyzing microcapsules. In some embodiments, means 56 may include the microparticle analytical device described above in reference to FIGS. 4-6. In particular, means 56 may include a system which includes adaptations to acquire images of a flowing fluid comprising the microcapsules as well as adaptations to measure the intensity of light transmitted through the microcapsules. It is noted, however, that microencapsulation system 20 is not restricted to the inclusion of such a device. In particular, microencapsulation system 20 may include any device or system configured to track, count, characterize and/or identify microcapsules.

In some embodiments, the characterization of microcapsules may include determining the size and/or shape of microcapsules within the production stream. In addition, the identification of microcapsules may include distinguishing different types of microcapsules and/or distinguishing microcapsules from debris or bubbles within the production stream. In this manner, means 56 may further be used to determine a concentration of different types microcapsules produced and processed within microencapsulation system 20. In general, the information obtained about the microcapsules (e.g., the size, shape, content and number) may be used for feedback control purposes to optimize the production of microcapsules from microencapsulation system 20. As shown in FIG. 1, means 56 for analyzing microcapsules may be arranged at the end of washing compartment 44. Alternatively, means 56 for analyzing microcapsules may be arranged in another region of washing compartment 44 or down stream from washing compartment 44.

In some cases, microencapsulation system 20 may further include central processing unit (CPU) 54 to control the operation of microencapsulation system 20. In particular, microencapsulation system 20 may include a dedicated microprocessor-based controller or a general-purpose computer configured to automate the operations of microencapsulation system 20 such that microcapsules may be fabricated and processed in a single continuous process. Consequently, the method described in reference to FIG. 3 below may, in some embodiments, be a computer-implemented method. As described below, CPU 54 may be used to control a variety of components within microencapsulation system 20 and, accordingly, may be coupled to the components of microencapsulation system 20 which it is configured to control. Such individual connections to the components, however, are not illustrated FIG. 1 to simplify the illustration of microencapsulation system 20. Instead, CPU 54 is shown coupled to microencapsulation system 20 by a dotted line to show a general connection to the components included within the microencapsulation system.

In some cases, CPU 54 may be configured to control the operation of microsphere dispensers 30 and 32 and/or pulsatile flow generators 34 and 36 to control the production of spherical droplets within inner chamber 26. In particular, CPU 54 may be configured to send program instructions with which to regulate the flow from microsphere dispensers 30 and 32, opening 38 and/or pulsatile flow generators 34 and 36 in order to produce microcapsules at a particular rate and size. In some cases, CPU 54 may be used to control the rate the washing solution is introduced into washing compartment 44 as well as the amount of washing solution that is recycled from washing compartment 44. In addition, CPU 54 may be configured to control the operation of means 56 for analyzing the microcapsules. Consequently, CPU 54 may, in some embodiments, be configured to simultaneously operate the microcapsule production unit of microencapsulation system 20, washing compartment 44 and means 56 to process the microcapsules in a continuous manner. In some cases, CPU 54 may be configured to change the flow rate of materials through dispensers 30, 32, and/or 46 based upon the analysis performed by means 56. In particular, CPU 54 may be adapted to provide a feedback control loop between the microcapsule production unit of microencapsulation system 20, washing compartment 44 and means 56 for analyzing the microcapsules. In this manner, the fabrication and processing of microcapsules may be automatically altered to produce microcapsules within design specifications of the product.

It is noted that although microencapsulation system 20 is adapted to produce, cure, wash and analyze a continuous flow of microcapsules, the system is not necessarily restricted to processing microcapsules through each of the four process steps. In particular, microencapsulation system 20 may be used for fewer process steps than for which the system has adaptations. In some embodiments, microencapsulation system 20 may be adapted to route microcapsules through bypasses such that one or more process steps may be averted. In other embodiments, microencapsulation system 20 may be adapted such that the microcapsules pass through the entire chamber, but are not processed with all adaptations of the system. In addition, microencapsulation system 20 may, in some embodiments, be configured to process microcapsules under sterile conditions. As noted above, microencapsulation system 20 may be used to form microcapsules for the medical and/or pharmaceutical industry. As such, special precautions may need to be taken to insure that the production of microcapsules is performed under sterile conditions in such applications. For example, components and/or subsystems may be included within microencapsulation system 20 to insure a continuous supply of steam is available for Steam-In-Place (SIP) sterilization of the system As noted above, FIG. 3 illustrates a flowchart of a method for processing microcapsules in a single continuous process. It is noted that the method described in reference to FIG. 3 may be conducted using any microencapsulation system configured to produce, cure, wash and analyze microcapsules in a single continuous flow and therefore, may be conducted using microencapsulation system 20 or a similar system thereof. As shown in FIG. 3, the method may include step 60 in which a continuous flow of microcapsules are produced within a suspended fluid. Such a step may include forming microcapsules with any number of materials and any structure, including but not limited to a microcapsule including an inner core and an intermediate shell, which is encapsulated by an outer membrane. The formation of the microcapsules may be conducted, for example, using the microcapsule production unit described above in reference to FIG. 1. In some embodiments, step 60 may specifically include dispensing substantially uniform droplets of fluids of substantially different viscosities, coating the substantially uniform droplets with an immiscible solution and forming an outer polymer shell around the coated fluid droplets. Such sequence of process steps may be particularly advantageous for systems which are adapted to form different types of microcapsules while also maximizing the packing density. It is noted, however, that the aforementioned sequence of process steps merely incorporates an exemplary embodiment of step 60 and, therefore, does not restrict the method described herein to such a process.

As shown in FIG. 3, the method may continue to step 62 in which a first fluid is separated from the suspended fluid while retaining the microcapsules within a second fluid of the suspended fluid. In reference to microencapsulation system 20, step 62 may be conducted as the fluid within chamber 28 traverses through separation baffle system 40. As noted above in reference to FIG. 1, the fluid may be used to suspend the microcapsules. In such an embodiment, the residual materials from inner chamber 26 or, more specifically from reservoirs 22 and/or 24 may be separated from the fluid while the microcapsules remain suspended within the polymer/solvent solution. As noted above, the separated materials may, in some embodiments, be recycled back through the system to form additional microcapsules. Consequently, the method depicted in FIG. 3 includes step 64 outlining such a recycling process. In some embodiments, however, step 64 may be omitted from the method. In such a case, the separated materials may be disposed.

FIG. 3 illustrates the continuation of the method to step 66 in which the microcapsules are passed from the suspended fluid directly into a washing solution. More specifically, step 66 may include removing the retained microcapsules from the suspended fluid and immediately rinsing the removed microcapsules with the washing solution. Such a process is described above in reference to transferring the microcapsules from the microcapsule production unit of microencapsulation system 20 into washing compartment 44. In some embodiments, the method may further include extracting at least some of the washing solution from the washing compartment as noted in step 70 of FIG. 3. Such an extraction process may, in some embodiments, continue onto step 72 in which the extracted washing solution is recycled in order to rinse other microcapsules. In such an embodiment, the method may include separating the residual fluid rinsed from the microcapsules from the washing solution as described in reference to phase separator 52 in FIG. 1. In yet other embodiments, the extracted washing solution may not be recycled back through the system. In such a case, step 72 may be omitted from the method described in reference to FIG. 3. In other embodiments, the washing solution may not be extracted from the washing compartment at all. Consequently, in some cases, step 70 may also be omitted from the method depicted in FIG. 3.

In either case, the method may further include analyzing the microcapsules as noted in step 68 of FIG. 3. Such a process is described above in reference to means 56 for analyzing microcapsules in microencapsulation system 20. In general, step 68 may include tracking, counting, characterizing and/or identifying microcapsules. In some embodiments, the characterization of microcapsules may include determining the size and/or shape of microcapsules within the production stream. In addition, the identification of microcapsules may include distinguishing different types of microcapsules and/or distinguishing microcapsules from debris or bubbles within the production stream. In this manner, step 68 may further include determining a concentration of different types microcapsules produced and processed within microencapsulation system 20. In any case, the microcapsules may, in some embodiments, be analyzed while suspended in a flowing fluid. As such, in some cases, step 68 may be conducted while the microcapsules are within the washing compartment of the microencapsulation system. In other embodiments, step 68 may be conducted when the microcapsules are in a different region of the system. In yet other cases, the microcapsules may be analyzed in a stagnant bath or in a region void of fluids. In any case, the method may further include step 69 for harvesting the microcapsules. Such a process may include collecting, sorting and/or packaging the microcapsules for further use.

It will be appreciated to those skilled in the art having the benefit of this disclosure that this invention is believed to provide a system and method for fabricating and processing microcapsules in a single continuous process as well as a system and method for analyzing microparticles in a flowing fluid. Further modifications and alternative embodiments of various aspects of the invention will be apparent to those skilled in the art in view of this description. For example, although embodiments of the microencapsulation system described herein are described as including a system which is configured to identify, count, characterize and/or track microparticles using a transmission of multi-wavelength light, a photometer and an imaging system, the microencapsulation system is not restricted to the inclusion of an analytical device with such a configuration. Similarly, the system described herein which is configured to analyze microparticles is not restricted to being used in applications in which microcapsules necessarily exist, much less in microencapsulation systems.

Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A device for analyzing microparticles, comprising:
   a chamber comprising an inlet and an outlet for respectively introducing and dispensing a flowing fluid comprising microparticles, the chamber configured to induce a laminar flow of fluid;
   a light source adapted to provide incident light through the chamber;
   a photometer configured to measure the intensity of light transmitted through individual microparticles; and
   an imaging system configured to acquire images of the flowing fluid within the chamber.

2. The device of claim 1, further comprising additional light sources configured to provide incident light through the chamber at different wavelengths than the light source.

3. The device of claim 1, wherein the chamber comprises a channel having a width between approximately 10 microns and approximately 1200 microns.

4. The device of claim 1, further comprising a microprocessor controller with a storage medium comprising program instructions for analyzing the measured light intensities and acquiring images of the flowing fluid.

5. The device of claim 4, wherein the storage medium further comprises program instructions for controlling fluid flow through the chamber.

6. The device of claim 1, wherein the imaging system comprises a magnification lens configured to enlarge the appearance of individual microparticles within the flowing fluid to be equal to or slightly larger than a pixel size of the images produced by the imaging system.

7. The device of claim 1, further comprising a moveable mirror system configured to reflect the light transmitted through the chamber to the imaging system.

8. The device of claim 1, wherein the device is configured to operate from battery power.

9. A microparticle flow sensor system, comprising:
   a chamber configured to induce a laminar flow of fluid comprising opposing optical view ports;
   one or more light sources configured to provide incident light through the optical view ports;
   an imaging system configured to acquire images of the fluid moving at laminar flow within the chamber; and
   a storage medium comprising program instructions executable using a processor for comparing measured intensities of light transmitted through the microparticles at different locations within the chamber.

10. The microparticle flow sensor system of claim 9, further comprising bandpass filters configured to simultaneously collect light intensity data from multiple wavelengths of the incident light.

11. The microparticle flow sensor system of claim 9, wherein the program instructions further comprise program instructions for distinguishing different types of microcapsules contained within the fluid.

12. The microparticle flow sensor system of claim 9, wherein the program instructions further comprise program instructions for distinguishing the microcapsules from debris microparticles.

13. The microparticle flow sensor system of claim 9, wherein the program instructions further comprise program instructions for determining a shape and size of the microparticles.

14. The microparticle flow sensor system of claim 9, wherein the program instructions further comprise program instructions for tracking the trajectory of particles within the fluid.

15. The microparticle flow sensor system of claim 9, wherein the program instructions further comprise program instructions for matching the measured light intensities with spectral characteristics of known microparticles.

16. A method for identifying and tracking microparticles in motion, comprising:
   flowing a fluid comprising microparticles in laminar motion through a chamber;
   transmitting light through the fluid within the chamber;

measuring the intensities of the light transmitted through the fluid;

imaging the fluid a plurality of times as the microparticles flow through the chamber; and comparing at least some of the intensities of light between different images of the fluid to detect and characterize the microparticles.

17. The method of claim 16, wherein the step of transmitting light comprises transmitting a spectrum of light through the fluid.

18. The method of claim 16, wherein the step of flowing the fluid comprises flowing the fluid at a rate between approximately 0.10 milliliters per minute and approximately 1.0 milliliters per minute.

19. The method of claim 16, wherein the step of comparing the intensities of light is used to identify and count the microparticles within the fluid.

20. The method of claim 16, further comprising comparing the different images of the fluid to:

calculate a time of flight of individual microparticles; and determine trajectories for the individual microparticles.

21. The method of claim 16, further comprising calculating sedimentation rates for the particles within the fluid.

22. The method of claim 16, further comprising calculating buoyancy rates for the particles within the fluid.

23. A device for analyzing microparticles, comprising:

a laminar-flow chamber comprising an inlet and an outlet for respectively introducing and dispensing a flowing fluid comprising microparticles;

one or more light sources adapted to provide incident light through the chamber;

a photometer configured to measure the intensity of light transmitted through the chamber;

an imaging system configured to acquire images of the flowing fluid within the chamber; and a storage medium comprising program instructions executable using a processor for:

analyzing the measured light intensities;

acquiring images of the flowing fluid; and identifying and characterizing the microparticles based upon the measured light intensities and acquired images.

24. The device of claim 23, wherein the one or more light sources are adapted to provide light of different wavelengths.

25. The device of claim 23, further comprising:

a moveable mirror system configured to reflect the light transmitted through the chamber to the imaging system; and a plurality of bandpass filters interposed between the moveable mirror system and the imaging system, wherein the bandpass filters are configured to simultaneously collect light intensity data from multiple wavelengths of the incident light.

26. The device of claim 23, further comprising a fluid subsystem configured to clean out the laminar-flow chamber.

* * * * *